United States Patent [19]

Larkin

[11] Patent Number: 4,895,570
[45] Date of Patent: Jan. 23, 1990

[54] LOCKING PORT SHROUD FOR PERITONEAL DIALYSIS TUBING CONNECTOR

[75] Inventor: Mark E. Larkin, Lindenhurst, Ill.

[73] Assignee: Abbott Laboratories, Abbott Park, Ill.

[21] Appl. No.: 189,640

[22] Filed: May 13, 1988

Related U.S. Application Data

[63] Continuation-in-part of Ser. No. 58,452, Jun. 5, 1987, abandoned.

[51] Int. Cl.$^4$ .............................................. A61M 5/00
[52] U.S. Cl. ..................................... 604/411; 604/905
[58] Field of Search .................................. 604/411–414, 604/905, 283, 29; 285/315, 319, 322

[56] References Cited

U.S. PATENT DOCUMENTS

| | | | |
|---|---|---|---|
| 4,161,949 | 7/1979 | Thanawalla | 604/411 |
| 4,511,359 | 4/1985 | Vaillancourt | 604/905 |
| 4,636,204 | 1/1987 | Christopherson et al. | 604/411 X |
| 4,655,764 | 4/1987 | Sato | 604/905 X |

Primary Examiner—John D. Yasko
Attorney, Agent, or Firm—Martin L. Katz

[57] ABSTRACT

A tubing connector adapted for peritoneal dialysis connections between tubing sets and containers of dialysate. The connection prevents inadvertent disengagement of tubing sets.

17 Claims, 3 Drawing Sheets

LOCKING PORT SHROUD FOR PERITONEAL DIALYSIS TUBING CONNECTOR

RELATED APPLICATION

This application is a continuation in part of co-pending application Ser. No. 07/058,452, filed on Jun. 5, 1987, now abandoned, naming the same inventor named herein, and assigned to the same assignee

BACKGROUND OF THE INVENTION

The present invention relates to tubing connectors adapted for peritoneal dialysis connections between tubing sets and containers of dialysate.

Peritoneal dialysis is a common mode of kidney dialysis for treatment of many forms of acute or chronic renal disease. Basically, dialysate is infused into the peritoneum where waste products (e.g. urea and creatinine) diffuse across the peritoneal membrane into the dialysate. The dialysate is then removed with the waste products. The infusion and removal of dialysate is called an exchange. Exchanges are repeated as needed to lower the concentrations of waste products in the blood to desired levels. Exchanges can be performed manually or by machine.

Manual forms of peritoneal dialysis, and some machine types of peritoneal dialysis require the use of tubing sets which "spike into" ports extending from containers of dialysate. The distal ends of such tubing sets have spikes which are inserted into tubular container ports, and puncture diaphragms extending across the ports. With the puncturing of the diaphragms, dialysate can flow from the container, through the port-spike connection, through the tubing set, and into the patient's peritoneum.

The problem with some spikes is that they can slip out of the ports, contaminating the spike and/or allowing dialysate to spill. Some manufacturers have provided clam shell-like protectors or screw-type shrouds to cover the spike-port connection, but such devices are difficult for physically impaired renal patients to operate.

Many chronic renal disease patients are impaired. Some have neuropathy, a degenerative state of the nerves, so they have poor coordination. Some experience extreme loss of muscle mass, so they lack the strength to perform simple connection procedures. Thus, it is a primary object of the invention to provide an improved peritoneal dialysis tubing connector, particularly one which can be more readily used by renal patients who are physically impaired or infirm.

SUMMARY OF THE INVENTION

The present invention relates to a peritoneal dialysis tubing connection which securely locks a pin to a bag port or first tube. The pin is connected to a second tube having an annular flange rearward of the pin, and carries a tubular collet. The tubular collet has a splayed end and a cored-out slot (preferably U-shaped) on its side. The inner portion of the slot defines a flexible finger which has a detent on its exterior surface. A tubular locking ring slides on the collet from a first to a second position and has an annular ridge-like cam surface on its interior. When the locking ring is initially advanced while in the first position, the cam engages the detent and flexible finger (without deflecting it inward). While at this first position, both the collet and locking ring are pushed to a stop position where the splayed end of the collet covers a portion of the port. In the stop position, the flexible finger of the collet is forward of the annular flange of the second tube. As additional force is applied to the locking ring, the locking ring is advanced through the intermediate position toward the second position and the cam surface deflects the detent bearing flexible finger inwardly. With the finger deflected, the collet cannot slide backward over the annular flange and off of the first tube. As the locking ring is slid to the second position over the splayed end, the splayed end is urged inwardly to engage and grip the port. At this second position the detent rides off of the cam surface while still maintaining the detent bearing flexible finger in a deflected position to prevent inadvertent removal of the collet from the port. Inadvertent retraction of the locking ring is also prevented because additional force is required to move the cam back over the detent when the locking ring is moved out of the second position.

In another embodiment, the collet and locking ring is provided with means for guiding the locking ring along a helical path from the first to the second position. The helical path is preferably defined by a helical thread and channel on the collet and locking ring.

Generally, the above features lock the connection together, preventing the pin from being inadvertently pulled from the port. Furthermore, engagement of the detent and cam in the first position prevents the locking ring from being inadvertently advanced before the splayed end of the collet can clear the gripping portion of the port. Likewise, when in the second position, engagement of the detent and cam prevents the locking ring from being inadvertently retracted, causing disengagement of the coupling. In addition, while the detent is deflected by the cam in the intermediate position, the flexible finger is deflected inwardly to prevent the spike from being prematurely disengaged from the port while the locking ring is being retracted.

DETAILED DESCRIPTION OF THE PREFERRED EMBODIMENT

Figure 1:
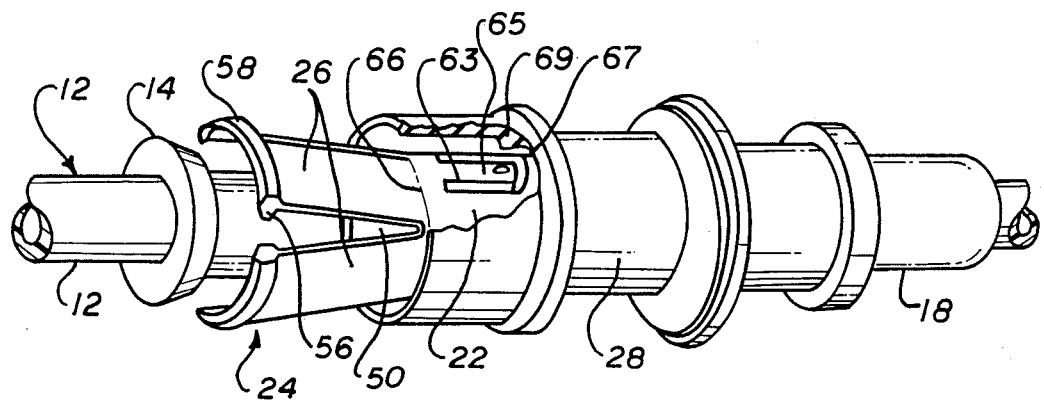
FIG. 1 is a perspective view of a collet in the unlocked, retracted position having a detent feature.
Figure 2:
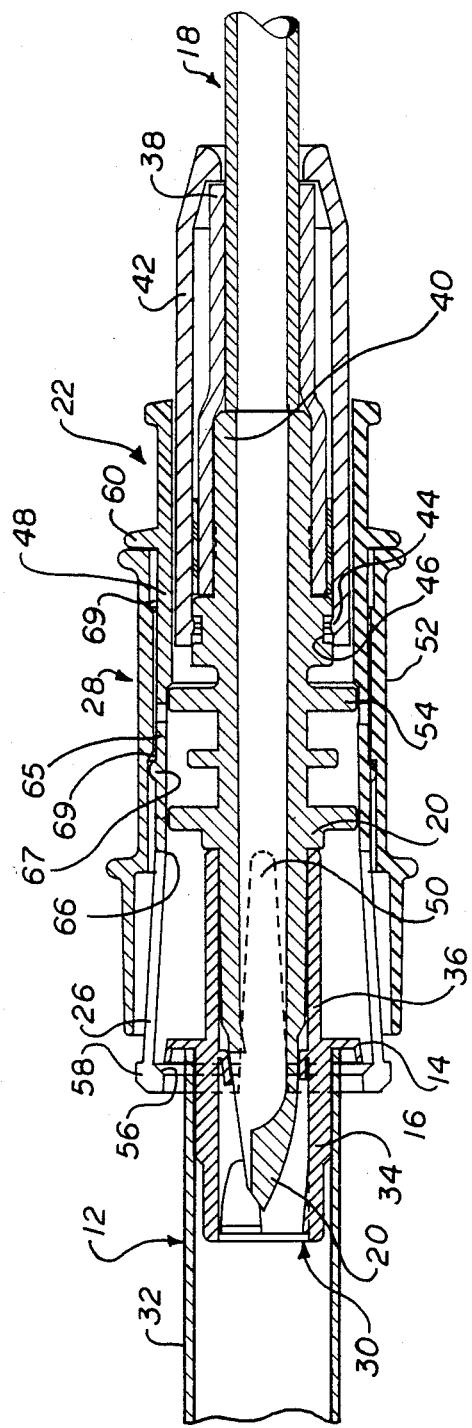
FIG. 2 is a cross-section of the connection of FIG. 1 in the unlocked retracted position.

Referring to FIGS. 1 and 2, the connection of the present invention includes a first tube 12 with a flange 14 and a pierceable diaphragm 16 disposed across the lumen of tube 12. A second tube 18 carries a pin 20 for piercing diaphragm 16 and connecting the two tubes together. Pin 20 carries a collet 22 having a splayed end 24 formed of a plurality of splayed segments 26. A tubular locking ring 28 is disposed slideably on collet 22. When pin 20 is "spiked into" diaphragm 16, collet 22 is advanced toward flange 14, and locking ring 28 is urged over splayed segments 26 to urge them inwardly to grasp flange 14 and lock the connection together.

Tube 12 is, in the preferred embodiment of this invention, a tubular port 30 on a container (glass or flexible plastic) of dialysate (not shown). However, the port can be on a bag of IV solution, parenteral solution or other containers with solutions useful in medical applications Port 30 includes an extruded tube 32 preferably made of a flexible PVC, and a tubular plug 34 preferably molded of a semi-rigid PVC inserted into the distal end of tube 32. Plug 34 is molded, and has diaphragm 16 integrally molded with it. Flange 14 is also integrally molded with it. Plug 34 also includes a tubular projection 36 which extends outwardly from tube 32, and guides pin 20 into the port when pin 20 is being inserted.

Second tube 18 is preferably the distal end of an administration tubing set (not shown) used in manual forms of peritoneal dialysis such as manual IPD or CAPD, or in machine peritoneal dialysis such as CCPD. Of course, in IV or other applications, other tubing sets can be used.

Second tube 18 is connected to pin 20 by sleeve 38 into which the distal end of tube 18 is telescopingly received and secured. The proximal end of pin 20 has a tubular shank 40 which is telescopingly received and secured into sleeve 38. A tubular shroud 42 overlays sleeve 38, and is mounted on pin 20 by internal detents 44 which extend into an annular recess 46 in pin 20. Sleeve 38 and shroud 42 protect the juncture of tube 18 and pin 20 from wear or kinking which may result if the pin is used on mechanical devices which assist the patient or hospital personnel in inserting the pin into the port.

Tubular collet 22 is slideably mounted on pin 20 and tube 18. Collet 22 can be advanced forwardly (FIGS. 3 and 6) toward the spiked end of pin 20, or retracted toward (FIGS. 1, 2, 4 and 5) or along (not shown) tube 18. The retraction of collet 22 allows the spiked end of pin 20 to be cleaned with a disinfecting solution, to be sterilized with ultraviolet light, or the like.

As previously explained, collet 22 has a main tubular body 48, and a splayed end 24 formed of a plurality of splayed portions 26. Each of splayed portions 26 is separated from the other by elongated recesses 50. Splayed portions 26 are oriented slightly outwardly from the longitudinal axis of collet 22 in their normal positions (FIGS. 1, 2, 4 and 5). In the embodiment shown in FIGS. 1-3, collet 22 also has a cored-out slot 63, preferably U-shaped, so that it defines a flexible finger 65 that is integral with the collet 22. Flexible finger 65 is located on the collet at a position slightly forward of a flange 54, and is preferably oriented with finger 65 pointing rearward. Thus, when flexible finger 65 is deflected radially inwardly, it will form an abutment which will engage flange 54 and prevent retraction. A detent means 67 is located on the exterior surface of the flexible finger 65 to engage with a cam 69 and assist in deflecting the flexible finger 65.

Collet 22 carries a tubular locking spool or ring 28. Locking ring 28 is slideable along collet 22 from a first position over body 48, to a second position over splayed segments 26. In the first position of locking ring 28, splayed segments 26 are angled outwardly where they cannot grip flange 14. However, when collet 22 is advanced to where flange 14 is surrounded by splayed segments 26, locking ring 28 can be advanced to the second position over splayed segments 26, forcing them inwardly (FIGS. 3 and 6) to retain or grasp flange 14. This locking prevents the pin from being withdrawn from the port.

Collet 22 has an internal shoulder 52 which abuts flange 54 on pin 20 when collet 22 is advanced toward the position where it can be locked. Flange 54 and shoulder 52 act as a locater against further advancement of collet 22. In addition, flange 54 and shoulder 52 prevent pin 20 from being pulled out of collet 22 and tube 12 when collet 22 is locked to flange 14.

Figure 3:
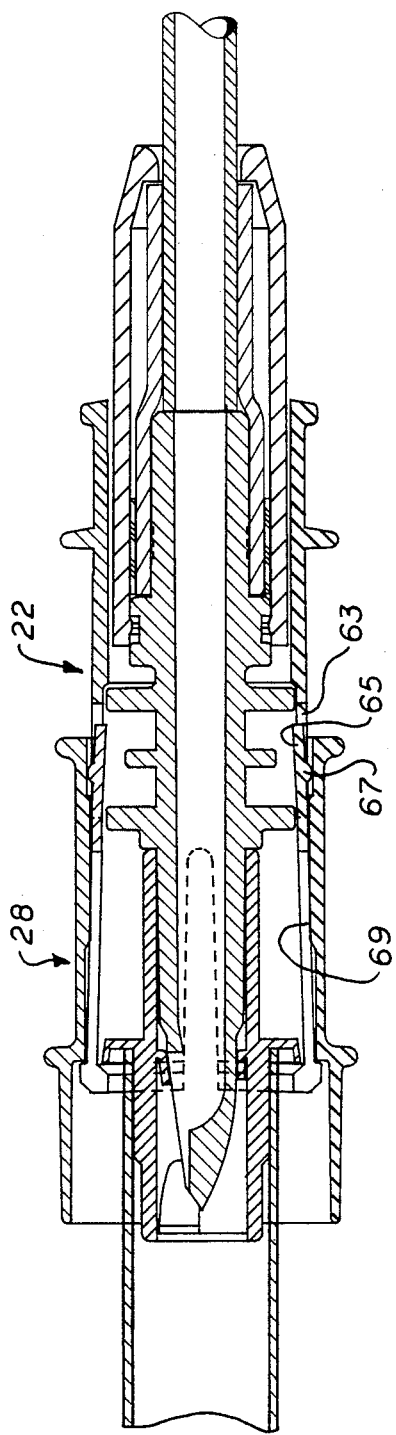
FIG. 3 is a cross-section of the connection of FIG. 1 in the locked forward position.
Figure 6:
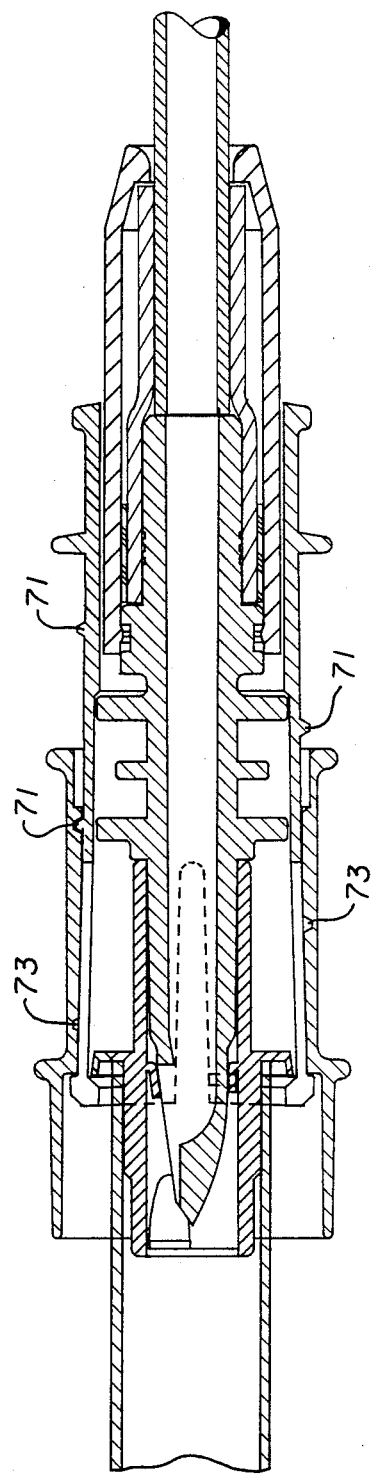
FIG. 6 is a cross-section of the connection of FIG. 4 in the locked forward position.

Each splayed segment 26 includes an internal shoulder 56 against which flange 14 abuts when splayed segments 26 are locked. Shoulders 56 prevent pin 20 from being pulled from tube 12 when collet 22 is locked (FIGS. 3 and 6).

An external shoulder 58 on each splayed segment 6 prevents locking ring 28 from sliding completely off splayed segments 26 when locking ring 28 is being advanced toward its locked position. An outwardly oriented flange 60 at the other end of collet 22 prevents locking ring 28 from being pulled completely off collet 2 when locking ring 28 is retracted to the unlocked position.

Locking ring 28 includes internal ridge-like cam 69 in the form of an internal, integrally formed annular ring. When the locking ring 28 is in the first position (retracted and unlocked) (FIGS. 1 and 2) cam 9 engages the detent 67 and resists further forward movement. In this first position, cam 69 does not deflect the detent means 67 and flexible finger 65. Thus, locking ring 28 remains in the first position until sufficient force is applied to the locking ring to cause the cam 69 to deflect the flexible finger 65. However, when it is desired to lock the connection after pin 20 is inserted into tube 12 and through diaphragm 16, locking ring 28 is grasped and advanced toward tube 12. Because cam 69 engages detent 67 and resists movement, locking ring 28 will initially drag collet 22 toward flange 14 as locking ring 28 is advanced.

When shoulder 52 engages flange 54 after collet 22 is fully advanced, application of additional force to locking ring 28 toward splayed segments 26 will cause the cam 69 to overcome the resistance of the detent bearing flexible finger 65. Locking ring 28 will therefore move from the first position to an intermediate position, causing cam 69 to deflect detent 67 and flexible finger 65 radially inwardly. When finger 65 is deflected, it projects inwardly to a point inside the diameter of the annular flange 54 on the second tube assembly. Since the finger is positioned forward of the flange 54 on the piercing pin, this projection prevents retraction of the collet. The locking ring 28 continues to be advanced forward into the second position, where locking ring 28 can be advanced over splayed segments 26 to lock them to flange 14. When locking ring 28 is in this locked second position (FIGS. 2 and 6), cam 69 releases the detent 67 and flexible finger 65, while still deflecting the finger sufficient to prevent retraction of the collet. Because additional effort is required for the cam to engage and override the force of the deflected finger, the locking ring 28 is retained in the second position.

Recess 66 is located at the junctures of each splayed segment 26 and the body 48 of collet 22. Thus, each recess 66 forms a flexure area allowing splayed segments 26 to be easily flexed inwardly when they are urged toward their locked positions.

With the features described in detail, the operation can be summarized. When a port is to be "spiked", pin 20 is grasped and forced into tube 12 and through diaphragm 16. Locking ring 28 and collet 22 are in the general positions shown in FIGS. 1 and 2, with cam 69 engaging detent 67. Locking ring 28 is grasped and moved toward tube 12, dragging collet 22 along with it. Shoulder 52 inside collet 22 will eventually hit flange 54 when collet 22 is fully advanced. Application of a small additional force will cause cam 69 to override the force of flexible finger 65 and force the finger to deflect inwardly. Locking ring 28 is advanced, with cam 69 continuing to deflect finger 65, causing the finger to project inwardly. In this position, the collet cannot be removed. The locking ring is advanced to the second position over splayed segments 26 until cam 69 releases detent 67, thus retaining the locking ring in position. In the second position, the flexible finger remains sufficiently deflected to prevent removal of the collet over the flange 54.

As locking ring 28 is advanced over splayed segments 26 before detent 62 engages recess 66, locking ring 28 will force the splayed segments 26 inwardly where they will engage and grip flange 14. When locking ring 28 abuts flanges 58, splayed segments 26 will be locked against flange 14, preventing the pin from being pulled from the port.

When locking ring 28 is in the locked position, it completely covers recesses 50 between splayed segments 26. This creates an enclosure around the pin-port connection which resists the accumulation and penetration of contaminants on the pin-port connection.

When locking ring 28 is retracted, the memory of splayed segments 26 causes them to spread outwardly and disengage from flange 14. Thus, pin 20 can be withdrawn from port 36. As the locking ring is retracted through the intermediate position, the flexible finger 65 remains deflected, thus preventing inadvertent disengagement of the collet from the tube before the locking ring can be moved into the first position.

One advantage of the present invention is that pins and ports need not have the same relative dimensions as they often did in the past. Previously, pins were provided with diameters so that when they were inserted into ports, tight interference fits were achieved. This prevented accidental withdrawal of the pin from the port. However, this tight interference fit also made it difficult for impaired patients to insert or withdraw the pin from the port.

Because the collet of this invention externally locks the pin into the port, no such tight interference is necessary. Only a slight interference—enough to form a liquid seal—is required. Thus, the pin is easily inserted and withdrawn from the port. A further advantage of the present invention is that the collet remains engaged with the second tube until the locking ring is fully retracted into the first position.

Figure 4:
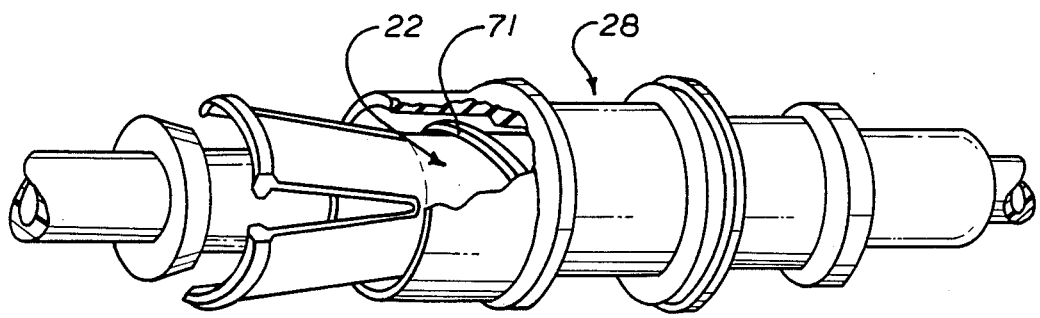
FIG. 4 is a perspective view of a collet with a helical guide means.
Figure 5:
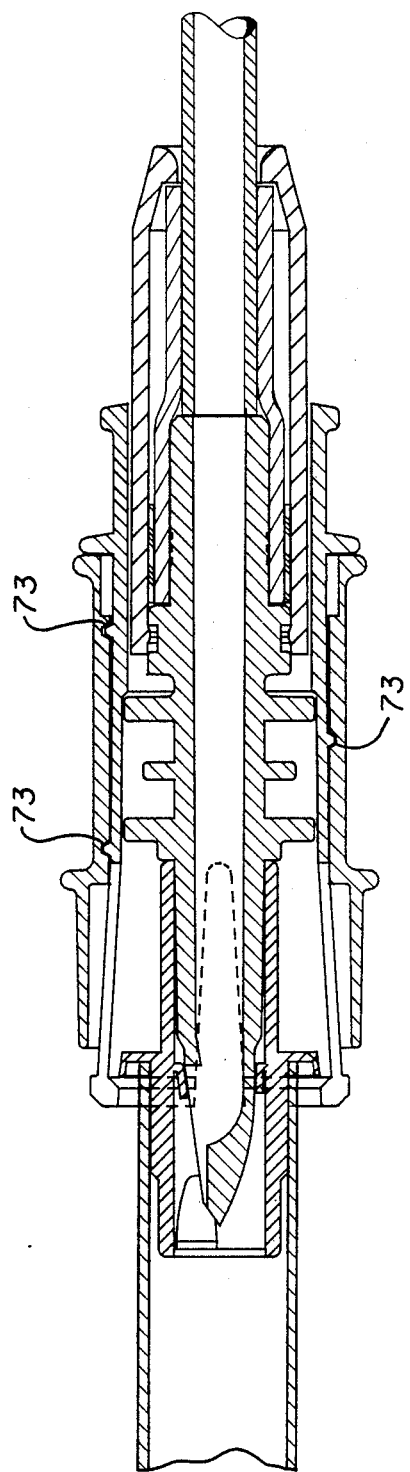
FIG. 5 is a cross-section of the connection of FIG. 4 in the unlocked retracted position.

In another embodiment, a connecting device is provided with means for guiding the locking ring from the first to the second position along a helical path. For example, the helical guide means may comprise a helical thread on either the collet or the locking ring, with a corresponding helical channel in the other. As illustrated in FIGS. 4-6, the collet 22 has a helical thread 71 on its exterior surface. Locking ring 28 has a helical channel 73 adapted to receive the helical thread 71 and guide the locking ring along a helical path from the first to the second position Preferably, the helical thread and channel arrangement is designed so that locking ring 28 requires only a single turn in order to advance it from the first to the second position.

While several embodiments of the invention have been described, modifications which do not part from the invention's scope will be readily apparent to one of ordinary skill in the art. All such modifications are intended to be covered by the accompanying claims.

What is claimed is:

1. A connection for medical tubing, comprising:
   a first tube having a flange and a pierceable diaphragm;
   a second tube having a piercing pin extending therefrom for piercing said diaphragm and an exterior annular flange rearward of said piercing pin;
   a tubular collet, having a splayed end, slideable along said second tube and said pin, further including a cored-out slot defining a flexible finger, said finger having a detent means on an exterior surface; and
   a tubular locking ring, slideable on said collet from a first position to a second position, including an annular cam on an interior surface;
   said annular cam being adapted to engage said detent means on said collet in said first position without forcing said flexible finger radially inwardly, depress said detent means radially inwardly to a position within the diameter and forward of said second tube annular flange while said locking ring slides intermediate from said first to said second position, and release said detent means in said second position while forcing said flexible finger radially inwardly.

2. The connection as recited in claim 1 wherein said pin has a shoulder against which said port abuts when said pin is inserted into said port.

3. The connection as recited in claim 1 wherein said collet has an outward flange at the end opposite said splayed end, and said splayed end has an outward projection, whereby said locking ring is slideably retained in said collet between said flange and said projection.

4. The connection as recited in claim 1 wherein said splayed end is formed by a plurality of splayed sections separated from each other by elongated recesses, said locking ring completely covering said recesses when locked to prevent material from collecting on said pin-first tube connection.

5. The connection as recited in claim 1 wherein said pin has an outwardly projecting flange, and said collet has inwardly projecting locator means which engages said outward flange on the pin when the collet is in the locked position.

6. The connection as recited in claim 1 wherein said pin has a sleeve connecting it to said second tube, and further includes a shroud overlaying said sleeve to protect said sleeve.

7. The connection as recited in claim 1 wherein said collet is molded from plastic, and said splayed end is molded with splayed segments oriented outwardly from the longitudinal axis of said collet.

8. The connection as recited in claim 7 wherein said collet segments having memory to return to their outward orientation when said locking ring is retracted from said segments.

9. A connection for medical tubing, comprising:
   a first tube having a flange and a pierceable diaphragm;
   a second tube having a piercing pin extending therefrom for piercing said diaphragm;
   a tubular collet, having a splayed end with gripper means, slideable along said second tube and said pin; and
   a tubular locking ring disposed slideably on said collet;

said collet and locking ring having means for guiding said locking ring helically from said first to said second position.

10. The connection as recited in claim 9 wherein said pin has a shoulder against which said port abuts when said pin is inserted into said port.

11. The connection as recited in claim 9 wherein said collet has an outward flange at the end opposite said splayed end, and said splayed end has an outward projection, whereby said locking ring is slideably retained in said collet between said flange and projection.

12. The connection as recited in claim 9 wherein said splayed end is formed by a plurality of splayed sections separated from each other by elongated recesses, said locking ring completely covering said recesses when locked to prevent material from collecting on said pin-first tube connection.

13. The connection as recited in claim 9 wherein said pin has an outwardly projecting flange, and said collet has inwardly projecting locator means which engages said outward flange on the pin when the collet is in the locked position.

14. The connection as recited in claim 9 wherein said pin has a sleeve connecting it to said second tube, and further includes a shroud overlaying said sleeve to protect said sleeve.

15. The connection as recited in claim 9 wherein said collet is molded from plastic, and said splayed end is molded with splayed segments oriented outwardly from the longitudinal axis of said collet.

16. The connection as recited in claim 15 wherein said collet segments having memory to return to their outward orientation when said locking ring is retracted from said segments.

17. The connection as recited in claim 9 wherein said helical guide means comprises said collet and said locking ring, one of said collet and said locking means having a helical thread and the other having a corresponding helical channel in which said helical thread travels.

* * * * *